(12) United States Patent
DiMuro

(10) Patent No.: US 9,106,684 B1
(45) Date of Patent: Aug. 11, 2015

(54) SYSTEM AND METHOD FOR PACKET PROFILING

(71) Applicant: JPMorgan Chase Bank, N.A., New York, NY (US)

(72) Inventor: Jeffrey D. DiMuro, Milford, CT (US)

(73) Assignee: JPMORGAN CHASE BANK, N.A., New York, NY (US)

( * ) Notice: Subject to any disclaimer, the term of this patent is extended or adjusted under 35 U.S.C. 154(b) by 0 days.

(21) Appl. No.: 14/298,477

(22) Filed: Jun. 6, 2014

Related U.S. Application Data

(63) Continuation of application No. 13/364,931, filed on Feb. 2, 2012, now Pat. No. 8,789,186.

(60) Provisional application No. 61/448,895, filed on Mar. 3, 2011, provisional application No. 61/453,345, filed on Mar. 16, 2011.

(51) Int. Cl.
*H04L 29/06* (2006.01)
*G06F 21/56* (2013.01)

(52) U.S. Cl.
CPC .......... *H04L 63/1408* (2013.01); *G06F 21/566* (2013.01)

(58) Field of Classification Search
CPC .......................... H04L 63/1429; G06F 21/566
USPC ...................................... 726/22, 24
See application file for complete search history.

(56) References Cited

U.S. PATENT DOCUMENTS

| | | | |
|---|---|---|---|
| 2006/0161986 A1* | 7/2006 | Singh et al. | 726/24 |
| 2009/0007102 A1* | 1/2009 | Dadhia et al. | 718/1 |
| 2010/0281539 A1* | 11/2010 | Burns et al. | 726/23 |

* cited by examiner

*Primary Examiner* — Hadi Armouche
*Assistant Examiner* — Dao Ho
(74) *Attorney, Agent, or Firm* — Hunton & Williams LLP

(57) ABSTRACT

Systems and methods for packet profiling are disclosed. According to one embodiment, a method for profiling incoming data packets for an organization includes the steps of (1) receiving, at an interface for a transport provider, a data packet; (2) using a computer processor, analyzing the data packet; (3) using the computer processor, based on the analysis, marking the data packet; and (4) transmitting the data packet to the organization.

14 Claims, 5 Drawing Sheets

SYSTEM AND METHOD FOR PACKET PROFILING

RELATED APPLICATIONS

This patent application is a continuation of U.S. patent application Ser. No. 13/364,931, now U.S. Pat. No. 8,789,186, filed Feb. 2, 2012, which claims priority to U.S. Provisional Patent Application Ser. No. 61/448,895, filed Mar. 3, 2011, U.S. Provisional Patent Application Ser. No. 61/453,345, filed Mar. 16, 2011; the disclosures of all of which are incorporated by reference in their entireties.

BACKGROUND OF THE INVENTION

1. Field of the Invention

The present invention generally relates to data packets, and, more particularly, to a system and method for packet profiling.

2. Description of the Related Art

Businesses and other organizations often rely on premise-based applications (firewalls, proxies, IDS/IPS, malware inspection, etc.) to inspect and hopefully prevent malicious and/or malformed data packets from entering their networks via, for example, http, ftp, smtp packets and other electronic protocols. Before a data packet is delivered to one of various ingress points within the organization's decentralized DMZs, the data packet is first processed by a third party transport provider or partner (for example, Internet service providers, such as AT&T, Verizon, etc.) that provides transport service and ensure efficient delivery of data from the organization's customers, partners, and others. These transport providers typically protect their own network from malicious intrusion and safeguard their own customers' data.

SUMMARY OF THE INVENTION

Systems and methods for packet profiling are disclosed.

According to one embodiment, a method for profiling incoming data packets for an organization includes the steps of (1) receiving, at an interface for a transport provider, a data packet; (2) using a computer processor, analyzing the data packet; (3) using the computer processor, based on the analysis, marking the data packet; and (4) transmitting the data packet to the organization.

In one embodiment, the data packet may be marked if it contains suspicious data. In another embodiment, the data packet may be marked if it does not contain suspicious data. In yet another embodiment, the data packet may be marked in a first way if it contains suspicious data, and in a second way if it does not contain suspicious data.

The method may further include the steps of (5) receiving, at an interface for the organization, the marked data packet; (6) determining a score for the data packet; (7) transmitting the data packet to an intended recipient if the score for the data packet meets a predetermined criteria; and (8) quarantining the data packet if the score for the data packet does not meet a predetermined criteria. The quarantine may be a sandbox. The data that is in quarantine may be further analyzed, and this analysis may be different from the analysis at the transport provider.

According to one embodiment, a method for profiling incoming data packets for an organization includes the steps of (1) receiving, at an interface for a transport provider, a data packet; (2) using a computer processor, analyzing the data packet to determine if the data packet contains suspicious data; (3) using the computer processor, transmitting the data packet to the organization using a first transmission network if the data packet contains suspicious data; and (4) using the computer processor, transmitting the data packet to the organization using a second transmission network if the data packet does not contain suspicious data.

According to one embodiment, a method for processing incoming data packets for an organization includes (1) receiving, at an interface for a transport provider, a result of a verification of an assessment of a data packet by an organization; (2) using a computer processor, updating an assessment procedure for the transport provider based on the result; (3) using the computer processor, analyzing a data packet using the updated assessment procedure; and (4) using the computer processor, based on the analysis, scoring the data packet. The updated assessment procedure to at least one third party.

According to one embodiment, a method for processing incoming data packets for a plurality of organizations, may include (1) receiving, at an interface for a transport provider, a report from each of a plurality of organizations, each report comprising a result of a verification of an assessment of a data packet by each organization; (2) using a computer processor, consolidating the reports; and (3) using the computer processor, updating an assessment procedure for the transport provider based on the result.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF PREFERRED EMBODIMENTS

Figure 1:
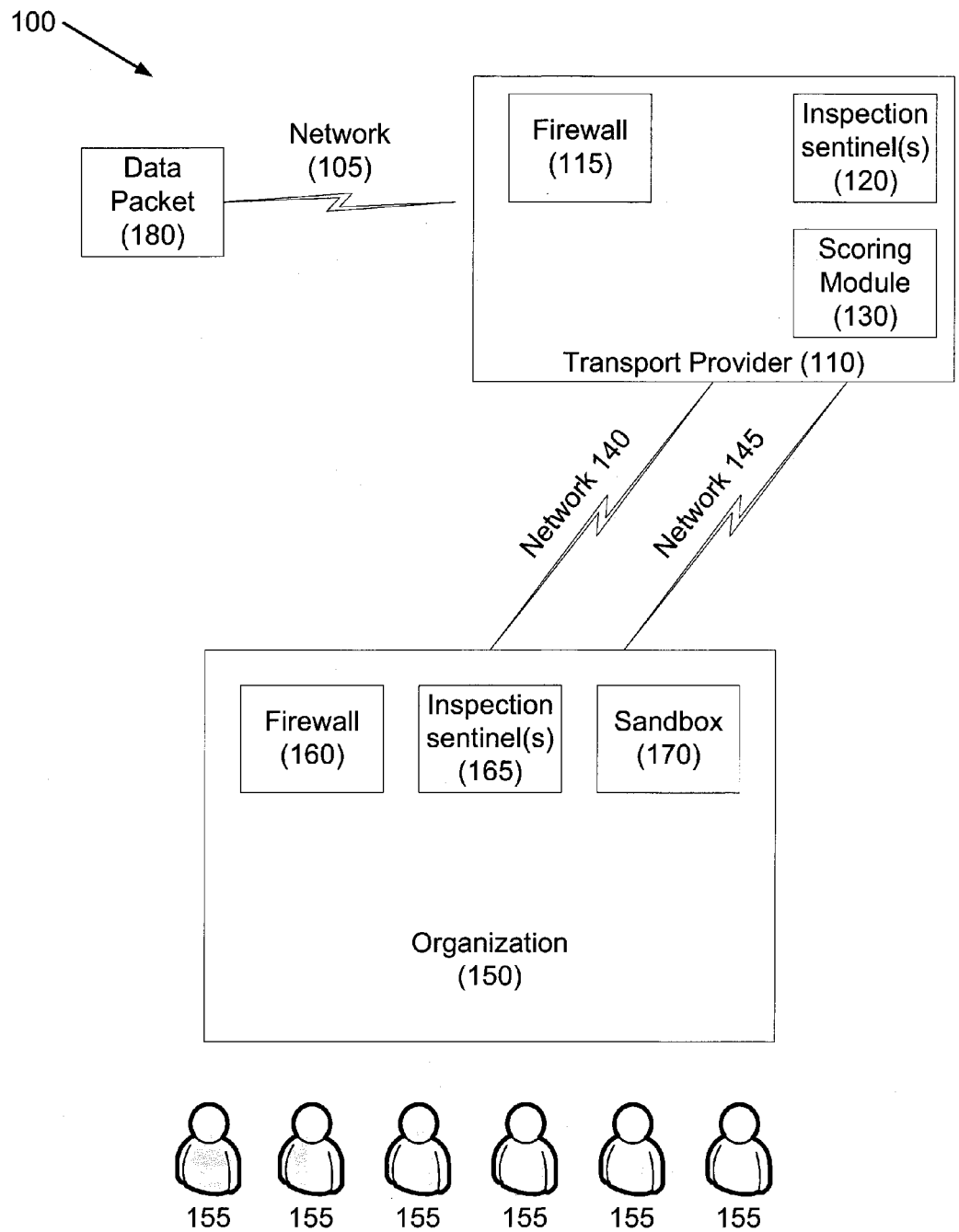
FIG. 1 is an illustration of a system for packet profiling according to one embodiment of the invention.

Several embodiments of the present invention and their advantages may be understood by referring to FIGS. 1-5, wherein like reference numerals refer to like elements.

The disclosures of U.S. patent application Ser. No. 13/323,277 and U.S. Provisional Patent Application Ser. No. 61/566,338, filed Dec. 2, 2011 are incorporated, by reference, in their entireties.

A transport provider may provide data to an organization. Examples of transport providers include internet service providers (ISP), wireless providers, etc. Rather than just providing "dumb" data transport services for incoming data packets to an organization, the transport providers may apply their individual and/or cumulative knowledge from, for example, previous and current events, and profile data packets before transporting them to the organization. The transport provider may be looking for malicious vectors, behavioral anomalies, known signature patterns, content types, attributes, etc. (or the potential therefore) within the data packets.

In one embodiment, the inspection sentinels may look for, separately or in addition to malicious data packets, specific content. For example, the inspection sentinels may look for packets containing access controls, such as digital rights management, copyrighted material, copy protection, digital locks, confidential information, privileged information, offensive material, or any other content of interest. The inspection sentinels may also identify data packets that are part of a very large data files, such as video files, or are part of a denial of service attack.

In one embodiment, the user may be able to specify one or more content type that the inspection sentinels are to identify.

Referring to FIG. 1, an illustration of an example of a system for packet profiling according to one embodiment of the invention is provided. In one embodiment, system 100 includes transport provider 110 and at least one organization 150. In one embodiment, transport provider 110 may be a third party, or it may be part of, or associated with, organization 150.

Transport provider or partner 110 may provide transport service and ensure efficient delivery of data to organization 150 via network 105. Network 105 may be any suitable network, including public, private, virtual, peer-to-peer, wired, wireless, etc. In one embodiment, network 105 may be the Internet.

In one embodiment, transport provider 110 may further transport data to its own customers. For example, transport provider 110 may function as an Internet Service Provider (ISP) for other businesses and individuals (not shown). In another embodiment, transport provider 110 may provide a device for providing the transport of data.

In one embodiment, transport provider 110 may include, for example, intrusion prevention system 115, inspection sentinel(s) 120, and scoring module 130.

In one embodiment, intrusion prevention system 115 may be any suitable device or set of devices that controls data transmission into a network. In one embodiment, intrusion prevention system 115 may be a firewall, such as a commercially-available firewall, or a custom firewall specific to transport provider 110.

Inspection sentinel(s) 120 may include tools that inspect a data packet for viruses, spam, or other malware. Inspection sentinel(s) 120 may further inspect a data packet for bot-nets, Trojans, blacklisted IPs, and other attack vectors.

In still another embodiment, inspection sentinel(s) 120 may inspect a data packet's content. In one embodiment, inspection sentinel(s) 120 may inspect the data packet for access control restrictions, such as digital rights management, copy protection, digital locks, confidential information, privileged information, offensive material, or any other content of interest. In another embodiment, inspection sentinel(s) 120 may inspect or evaluate the data packet for the size of the data file of which the data packet is a part.

In one embodiment, inspection sentinel(s) 120 may include commercially-available sentinels, or may include custom inspection sentinel(s) specific to transport provider 110 or the type of network traffic expected to be received by transport provider 110. Examples of inspection sentinel(s) include firewalls (e.g., from Cisco Systems, Juniper Networks, Check Point Software Technologies, Barracuda Networks, etc.), anti-virus software and applications (e.g., Symantec AntiVirus, McAfee VirusScan, etc.) and others.

In one embodiment, inspection sentinel(s) 120 may clean incoming data packets 180 as necessary and/or desired.

Scoring module 130 may analyze and score incoming data packets 180. In one embodiment, scoring module 130 may assign a score to each incoming data packet 180. In another embodiment, scoring module 130 may assign a score only to certain incoming data packets 180. Examples of how data packets 180 may be scored is discussed below.

In one embodiment, scoring module 130 may score the data packet based on what the data packet could be combined with. For example, the data packet itself may not be harmful, but when combined with another data packet, may be harmful.

In another embodiment, scoring module 130 may score data packet 180 according to content of the data packet. For example, data packet 180 may be scored based on the size of the data file of which it is a part, whether it contains access controls, etc. This score may be a separate "content score," or it may be included in the score based on the malware/malicious data packet inspection.

Organization 150 may be any suitable organization that may use transport provider 110 for the delivery of data packets 180. In one embodiment, organization 150 may be any suitable business, corporation, government agency, not for profit, community, etc. In one embodiment, organization 150 may include an individual. Organization 150 may support a plurality of users 155.

In one embodiment, organization 150 may include intrusion prevention system 160, inspection sentinel(s) 165, and sandbox or quarantine area 170. Organization 150 may further include web application firewalls (WAFS, not shown), reverse proxies (not shown), anti-malware agents (not shown), etc.

In one embodiment, intrusion prevention system 160, like intrusion prevention system 115, may be any suitable device or set of devices that controls data transmission into organization 150's network.

Organization 150 may provide one or more inspection sentinel 165. Like inspection sentinel(s) 120, inspection sentinel(s) 165 may include tools that inspect a data packet for viruses, spam, or other malware. Inspection sentinel(s) 165 may include commercially-available sentinels, or they may include custom inspection sentinel(s) specific to organization 150 or the type of network traffic expected to be received by organization 150.

In one embodiment, inspection sentinel(s) 165 may be the same as inspection sentinel(s) 120 used by transport provider 110. In another embodiment, inspection sentinel(s) 165 may be different from inspection sentinel(s) 120 used by transport provider 110.

Organization 150 may further provide sandbox or quarantine area 170. Sandbox 170 may provide a set of resources for some, or all, of data packets 180 to execute or be evaluated within, such as a controlled portion of disk space or memory. Network access, the ability to inspect the host system or read from input devices may be disallowed or heavily restricted.

Transport provider 110 and organization 150 may communicate via network 140 and/or network 145. In one embodiment, networks 140/145 may be the Internet.

In one embodiment, networks 140/145 may be a private network, including virtual private networks. In another embodiment, one or both of networks 140/145 may be a secure network. In still another embodiment, one or both of networks 140/145 may be a unsecure network.

In one embodiment, networks 140/145 may provide multiple connections, or "pipes," between transport provider 110 and organization 150.

In still another embodiment, networks 140 and 145 may be the same communication medium (e.g., Ethernet). In another embodiment, networks 140 and 145 may be different communication mediums. For example, network 140 may provide Ethernet communications, while network 145 may provide SMS communications. Other communication mediums, such as wired, wireless, cellular, or other communications modalities, or combinations thereof may be used as necessary and/or desired.

Data packet 180 may be any suitable data packet that can be transmitted on a network, such as an IP data packet (e.g., IPv4, IPv5, IPv6), a packetized elementary stream (PES) data packet, or any other generic unit of information.

Figure 2:
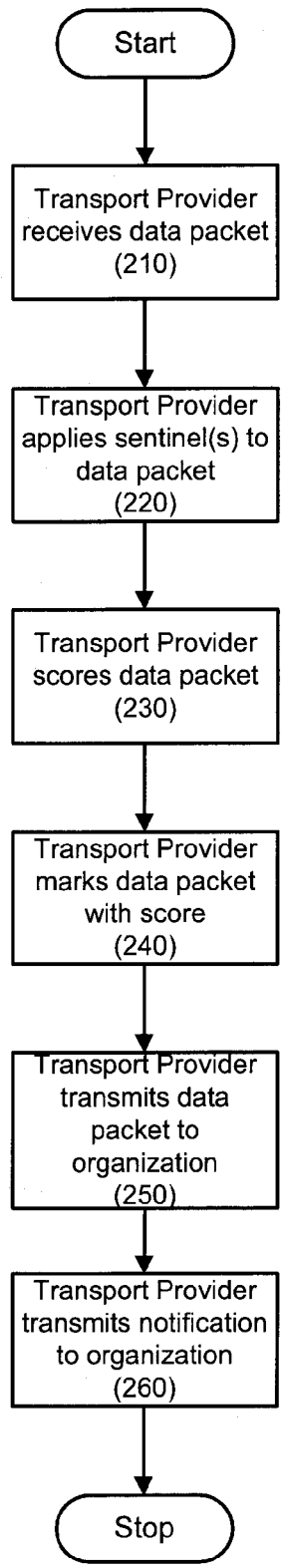
FIG. 2 is a flowchart depicting an example of a method for packet profiling according to one embodiment of the invention.

Referring to FIG. 2, a flowchart depicting an example of a method for packet profiling according to one embodiment of the invention is provided. In step 210, the transport provider may receive a data packet that is intended for the organization or an intended recipient.

In step 220, the transport provider may inspect the data packet. This may include applying one or more inspection sentinels to the data packet. In one embodiment, the transport provider may use the same inspection sentinel(s) that it uses on its own incoming data packets. In another embodiment, the transport provider may apply additional or different inspection sentinel(s). In one embodiment, inspection sentinel(s) that are specific to the organization, the business of the organization, the geography of the organization, etc. may be used. In one embodiment, the inspection sentinel(s) may use a series of standard and ad hoc (customized) policies and rules to look for certain behavioral traits.

In step 230, the transport provider may score the data packet. This may be based on the outcome of the application of the inspection sentinel(s). For example, the packets may be scored as high, medium, or low risk; on a risk scale (e.g., ranging from 1-5, 0 to 100, etc.); as clean/unclean, of interest/not of interest, protected/not protected, etc. In one embodiment, the scoring may reflect a route or a destination for the data packet, such as "pipe 1" or "sandbox." Any suitable scoring scheme may be used as necessary and/or desired. In one embodiment, the inspection sentinel(s) may use a series of standard and ad hoc (customized) policies and rules to look for certain behavioral traits, such as viruses, malware, trends, source, etc.

Other factors may be considered in scoring the data packets. In one embodiment, the source of the data packet may be considered. For example, if the source is trusted, this may reduce the likelihood that the data packet will be scored above a certain level of risk.

In another embodiment, the content of the data packet may be considered in scoring the data packet. In one embodiment, the content score may be part of a general score for the data packet. In another embodiment, the content score may be separate from the score associated with the malicious software score for the data packet. In still another embodiment, the content score and/or the malicious software score may be provided.

The content may be analyzed to determine if the content of the data packet contains any access control restrictions, such as digital rights management, copyrighted material, copy protection, digital locks, confidential information, privileged information, offensive material, or any other content of interest. In another embodiment, the size of the data file of which the data packet may be part of may be considered. For example, a data packet that is part of a very large video file may be scored differently from a data packet that is part of a small image file.

The scoring may also account for what the data packet could be combined with. For example, a data packet may be a piece of a larger malicious software puzzle that is comprised of two or more data packets, and may be scored to reflect the possibility of such a combination.

An example scoring scheme is as follows. If the source of a data packet is a known source of malware or viruses, blacklisted, etc. the score may be increased by 50. If the data packet is determined to have or be part of a virus, Trojan, etc. that can be cleaned, the score may increase by 5. If the virus, Trojan, etc. cannot be cleaned, the score may increase by 30.

As noted above, any useful scale (numeric, letter, color, temperature, code word, etc.) may be used in scoring the data packet as necessary and/or desired.

When the data packet is received at the organization, the organization's intrusion prevention system may apply its policies to determine whether the score exceeds a threshold for distributing the data packet to its intended recipient.

In one embodiment, any digital signature that may be associated with a data packet may be considered. For example, if the data packet has been previously scored and digitally signed, the data packet may not be re-scored.

In another embodiment, the date and/or time of the prior scoring may be considered. For example, if a data packet was scored more than a predetermined number of days ago, that score may be considered reliable. If the scoring is more recent, the data packet may be re-scored.

In one embodiment, the transport provider may be a type of a certificate authority, and may issue a certificate with regard to the scoring of the data packets. These certificates may be accepted by other transport providers and organizations.

In one embodiment, the transport provider may process data packets for other transport providers and organizations, and may provide a score, digital signature, and/or certificate for the processed data packets.

In step 240, the transport provider may associate the score with the data packet. This may be accomplished in any suitable way. For example, in one embodiment, the data packet may be marked with the score. In another embodiment, an additional data packet containing the score may be appended to the scored data packet. In still another embodiment, the score may be stored in a separate location and may be accessed using a packet identifier.

In one embodiment, more than one packet may be scored together. For example, ten packets of a larger data file may be assigned the same score.

In one embodiment, the packet itself may be marked with the score by modifying a bit within the packet. The bit may be in, for example, a header field of a packet. An IPv6 packet header, for example, includes the following fields: source address; destination address; version/IP version; packet priority/traffic class; flow Label/QoS management; payload length in bytes; next header; and time to live (TTL)/hop limit. In one embodiment, any unused bit (or bits) in any of these fields may be used as necessary and/or desired. In another embodiment, leading or trailing bit or bits may be used as necessary and/or desired.

In another embodiment, an unused, leading, or trailing bit of the payload may be used. In still another embodiment, a bit (or bits) may be appended to the header or payload.

In one embodiment, the bit or bits may be encrypted. This may be done by applying a cryptographic hash function to the bit or bits.

In another embodiment, a digital signature may be included in, or appended to, the packet. In one embodiment, the digital signature may provide an identification of the entity that is marking the data packet, a time and date of the marking, an expiration of the marking, the score and/or classification of the contents of the packet, and any other useful information. In one embodiment, the digital signature may further include a unique identifier that may be used to track the data packet or retrieve information about the packet.

In one embodiment, the objective of the inclusion of the digital signature is to draw some correlation between the type of data sent, by whom it was sent, the source, and destination.

Other security techniques or mechanisms may be used as necessary and/or desired.

In one embodiment, the transport provider may clean data packets having a certain score or risk level. For example, the transport provider may clean data packets that are scored as high risk. This cleaning may be in addition to, or in place of, scoring the data packet. In another embodiment, the transport provider may not clean the data packet so that the packet is transmitted to the organization in the same condition as it was received at the transport provider except for the scoring.

In step 250, the transport provider may transmit the scored data packet to the organization. In one embodiment, the scored data packets may be transmitted over a non-secure data channel. In another embodiment, the scored data packets may be transmitted using a secure data channel. In still another embodiment, a combination of a secure data channel and a non-secure data channel may be used. The use of these channels may be based on, for example, the score of the data packet.

In step 260, the transport provider may send a separate notification to the organization regarding the status of the data packet. In one embodiment, a separate notification may be transmitted for each data packet scored and/or transmitted. In another embodiment, a notification may be sent for a plurality of data packets. The notification may be sent periodically (e.g., hourly, daily, weekly, monthly).

The notification may include, for example, an identification of the data packet(s), the score or risk of the data packet(s), the date/time of processing, an identification of the sentinel(s) applied, any specific risks identified in the packet(s) (e.g., the identity of a virus), any action taken (e.g., cleaned the data packet, transmitted the data packet), etc.

In one embodiment, the source and destination information may be noted as correlation techniques within the inspection sentinel(s) and/or inspection sentinel(s) policies may be applied.

In one embodiment, the notification may be sent to the organization using the same communication channel that is used to deliver the data packets. In another embodiment, the notification may be sent using a different communication channel than the one that is used to transmit data packets.

In one embodiment, the notification may be sent by email. In another embodiment, the notification may be posted to a website. In still another embodiment, the notification may be sent by text (SMS) message. In another embodiment, the notification may be sent by facsimile. Other methods of transmitting the notification, e.g., voice, regular mail, etc. may be used as necessary and/or desired.

In one embodiment, a summary may be sent to the organization periodically. The summary may include, for example, the number of data packets processed during the period, a statistical analysis of the data packets processed, the results of the scoring/marking of those packets, any trends identified during this period, etc.

In one embodiment, the transport provider may also apply its scoring to outbound data packets, and may provide a report to the organization on the status of its outgoing data packets. For example, the organization may report the number of data packets processed during the period, the number of data packets with a score exceeding a threshold, etc. In one embodiment, the transport provider may inform the organization if an outbound data packet was not "clean." In one embodiment, the transport provider may also take steps to remedy the transmission of "unclean" data packets, such as ceasing the transmission of only the unclean outbound data packets from the organization. In another embodiment, the transport provider may cease transmission of any outbound data packets from the organization.

In one embodiment, the transport provider may inform the organization of any content-related issues. For example, the organization may be informed if data packets containing access control restrictions are received. The transport provider may also inform an authority (e.g., law enforcement), an Internet service provider (ISP), the content owner, etc. of the receipt of such data packets, or it may restrict or discontinue transport service as necessary and/or desired.

In one embodiment, the reporting may be bi-directional. In another embodiment, the reporting may be to a third party.

Figure 3:
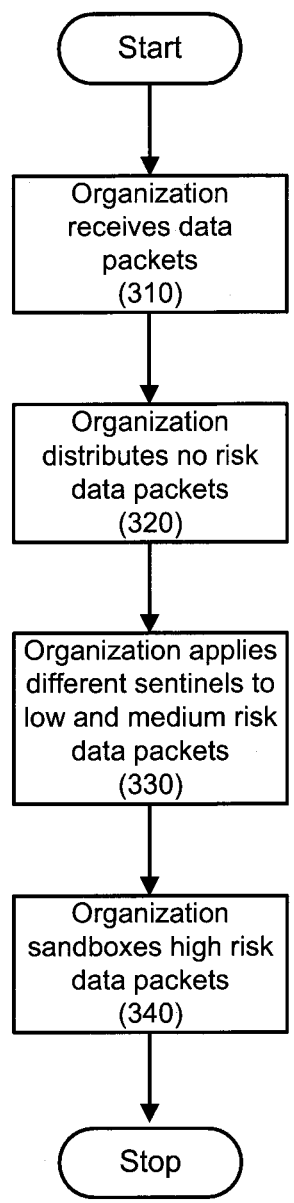
FIG. 3 is a flowchart depicting a method of processing received profiled data packets according to one embodiment of the invention.

Referring to FIG. 3, a method of processing the received profiled data packets is provided. In step 310, the organization receives the scored data packets.

In step 320, the organization may distribute data packets that have been scored as having no risk to their intended recipients. This may also include data packets that have been cleaned by the transport provider.

In one embodiment, prior to distribution, the organization may apply at least one inspection sentinel to the data packets scored as no risk. In one embodiment, a different inspection sentinel from that applied by the transport provider may be used.

In one embodiment, the organization may apply at least one inspection sentinel to all incoming data packets. In another embodiment, the organization may apply at least one inspection sentinel to randomly-selected incoming data packets to ensure that the transport provider is applying inspection sentinels. In another embodiment, the organization may periodically apply at least one inspection sentinel incoming data packets. Other arrangements may be used as necessary and/or desired.

If the data packets are confirmed to have no risk, they may then be distributed to the intended recipient.

In one embodiment, data packets marked as low risk may also be distributed to their intended recipients. The decision on whether a suspicious data packet is distributed may be based on the reason the data packet is suspicious, an organization's risk tolerance, the ability of individual workstations to handle suspicious data packets, etc.

In another embodiment, a risk standard may be applied to multiple organizations in determining whether or not to distribute the data packet.

In one embodiment, prior to distribution, the organization may apply at least one inspection sentinel to the data packets scored as low risk. In one embodiment, a different inspection sentinel from that applied by the transport provider may be used.

In step 330, the organization may apply at least one inspection sentinel data packets that have not been distributed. In one embodiment, this may be applied to low risk, medium risk, high risk, or any combinations, of data packets. In one embodiment, a different inspection sentinel from that applied by the transport provider may be used.

In one embodiment, the organization may apply its sentinel(s) to some or all data packets received from the transport provider. In one embodiment, the organization may collect data regarding the data packets and the effectiveness of the inspection sentinel(s) used by the transport provider. That data may be used to improve the effectiveness of the inspection sentinel(s) used by the transport provider, by the organization, and by third parties.

In one embodiment, if the organization determines that a data packet that was scored to not contain malicious data does contain malicious data, the organization may take any steps that are necessary and/or desired. For example, the organization may evaluate all incoming data packets until the transport provider remedies the inspection sentinels. In another embodiment, the organization may alter the score or risk threshold for evaluating incoming packets. In another embodiment, the organization may isolate itself from outside networks. In another embodiment, the organization may inspect all available data packets within the organization.

In step 340, the organization may "sandbox" any data packets that, for example, it cannot clean, are scored above a certain risk level, are marked suspicious, may be from a specific source, are potentially suspicious, etc. In one embodiment, data packets that are received from known bad IP addresses, such as where an incoming email packet would fail Sender Policy Framework (SPF) and/or DomainKeys Identified Mail (DKIM) validation checks.

A sandbox may provide a set of resources for the data packets to execute or be evaluated within, such as a controlled portion of disk space or memory. Network access, the ability to inspect the host system or read from input devices may be disallowed or heavily restricted. In one embodiment, the organization may sandbox data packets that were above a threshold risk level regardless of whether they were cleaned.

In another embodiment, the data packets may be quarantined and delivered to the intended recipient via a web service.

In still another embodiment, the data packets may be provided to a third party for processing.

In one embodiment, the sandbox may contain, for example, advanced filters, Intrusion Prevention Systems (IPS) switches, etc.

In one embodiment, the intended recipient may be sent a notification of the receipt of the data packet that has been sandboxed, and may be sent a link to the data packet in the sandbox for inspection. Notification may be, for example, by email, text message, voice message, etc.

In one embodiment, if the organization determines that the sandboxed data packet does contain malware or malicious content, the organization may validate the transport provider's score. In one embodiment, the organization may indicate its validation with, for example, a digital signature.

In one embodiment, the organization may inform the transport provider of any "false positives"—data packets scored as suspicious that were ultimately determined to not contain malware, malicious software, etc.—in order to improve the transport provider's ability to score, mark, etc. the data packets.

In one embodiment, the organization may provide reporting of malicious data packets that were not detected by the applied sentinel(s) to the transport provider, the sentinel provider, other organizations, etc. This may increase the effectiveness of screening by not only the transport provider and the organization, but by others. It may also serve as a sort of feedback loop to the transport provider that may receive only the affected packet, or the entire data file that contains the affected packet, by which the transport provider may improve its inspection of incoming data packets.

In one embodiment, the organization, the transport provider, third party, etc. may sell, or make available, the results of its scoring data packets as a separate product. This may serve as a proactive method for addressing malicious data packets, and may, to a certain extent, predict trends in malicious alteration of data packets. The data from more than one organization may be consolidated.

In one embodiment, the organization may remove the marking from the data packets. This may be done when the data packets are processed by the organization, when they are transmitted from the organization, etc.

In another embodiment, the organization may retain the transport provider's data packet marking. This may provide third parties with an indication of the risk level associated with the data packet at the time of marking.

In still another embodiment, the organization may digitally sign the data packet as being accessed. The organization may further digitally sign the data packet with, for example, information concerning the date/time received, organization identification information, whether the packet was opened without issue, etc. In another embodiment, this information may be associated with a packet identifier and stored in a database.

In one embodiment, the organization may digitally sign the data packet to validate the score. In another embodiment, the organization may provide its own score to the data packet. In one embodiment, the organization may only sign or score the data packet when it leaves the organization.

In another embodiment, the transport provider may score some or all outgoing data packets from the organization. In one embodiment, the data provider may clean any data packets that are scored to potentially contain malicious software. The transport provider may report any cleaning to the organization and the organization may take any necessary steps to limit the spread of any contaminated data packets as necessary and/or desired.

In one embodiment, the transport provider may adjust its fee schedule based on any additional cleaning required for outgoing data packets.

Figure 4:
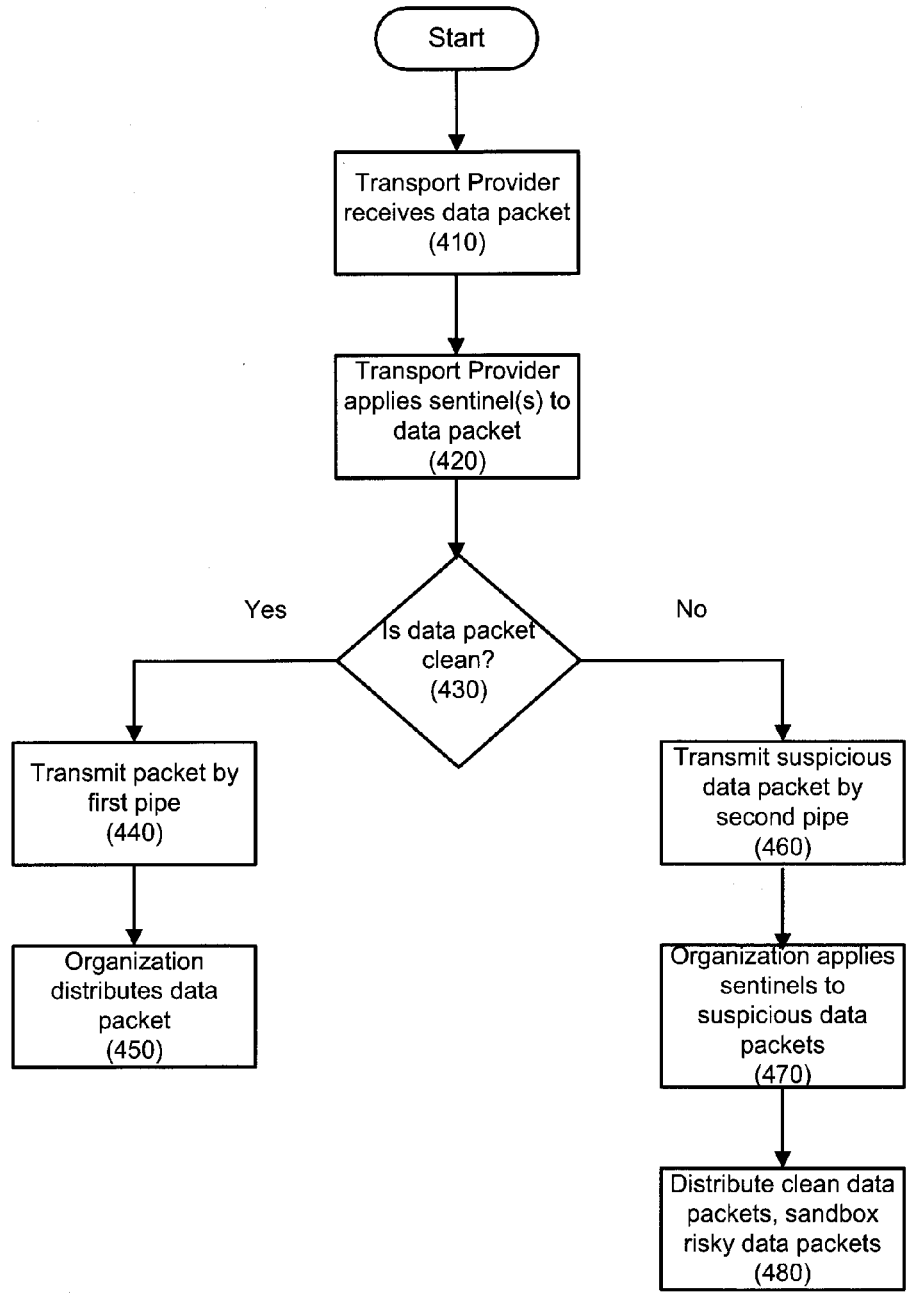
FIG. 4 is a flowchart depicting an example of a method for packet profiling according to another embodiment of the invention.

Referring to FIG. 4, an example of a method for packet profiling according to another embodiment of the invention is provided. In step 410, the transport provider may receive a data packet intended for the organization, and, in step 420, the transport provider may apply at least one inspection sentinel to the data packet. These steps may be similar to steps 210 and 220, above.

In step 430, the transport provider determines if the data packet is "clean," or if it is a no risk data packet. If it is, in step 440, the transport provider transmits the clean data packet to the organization by a first data "pipe" (or channel). In step 450, the organization may distribute data packets received via the first data "pipe" without further analysis.

In one embodiment, the organization may still apply inspection sentinel(s) to the data packets received via the first data "pipe" to, for example, check the effectiveness of the transport provider's inspection sentinel(s) and to gather other data.

In one embodiment, data packets that are not clean may be transmitted by the first data "pipe." This may be because the organization can clean the data packets, the data packets do not exceed a scoring threshold, etc.

If the data packet is not clean, in step 460, the suspicious data packets are transmitted by a second "pipe" to the organization.

In step 470, like in step 330, the organization may apply at least one inspection sentinel(s) to the other data packets. In one embodiment, this may be applied to low risk, medium risk, high risk, or any combinations, of data packets. In one embodiment, inspection sentinel(s) that are different from those applied by the transport provider may be used.

In one embodiment, the organization may apply at least one inspection sentinel to all incoming data packets. In another embodiment, the organization may apply at least one inspection sentinel to random incoming data packets. In another embodiment, the organization may periodically apply at least one inspection sentinel to incoming data packets.

In step 480, like step 340, the organization may "sandbox" any data packets that it cannot clean. In one embodiment, the organization may sandbox high risk data packets regardless of whether they were cleaned.

In one embodiment, all suspicious data packets may be sandboxed.

In one embodiment, the recipient of a data packet that has been sandboxed may be notified by, for example, email, SMS, phone, or any other suitable communication mechanism.

In one embodiment, a three "pipe" approach may be used. The first "pipe" may be used to send no-risk or clean data packets; the second may be used to send, for example, low-risk data packets that would go through normal filtering at the organization. In one embodiment, these may be data packets that could be cleaned by the transport provider, but, to maintain packet integrity, are not cleaned.

The third "pipe" may be used to send medium and high risk data packets, and may be sent to a sandbox for additional inspection.

Any number of "pipes" or data channels may be used as necessary and/or desired.

In one embodiment, the organization and/or the transport provider may provide reporting based on the data packets received and analyzed.

Figure 5:
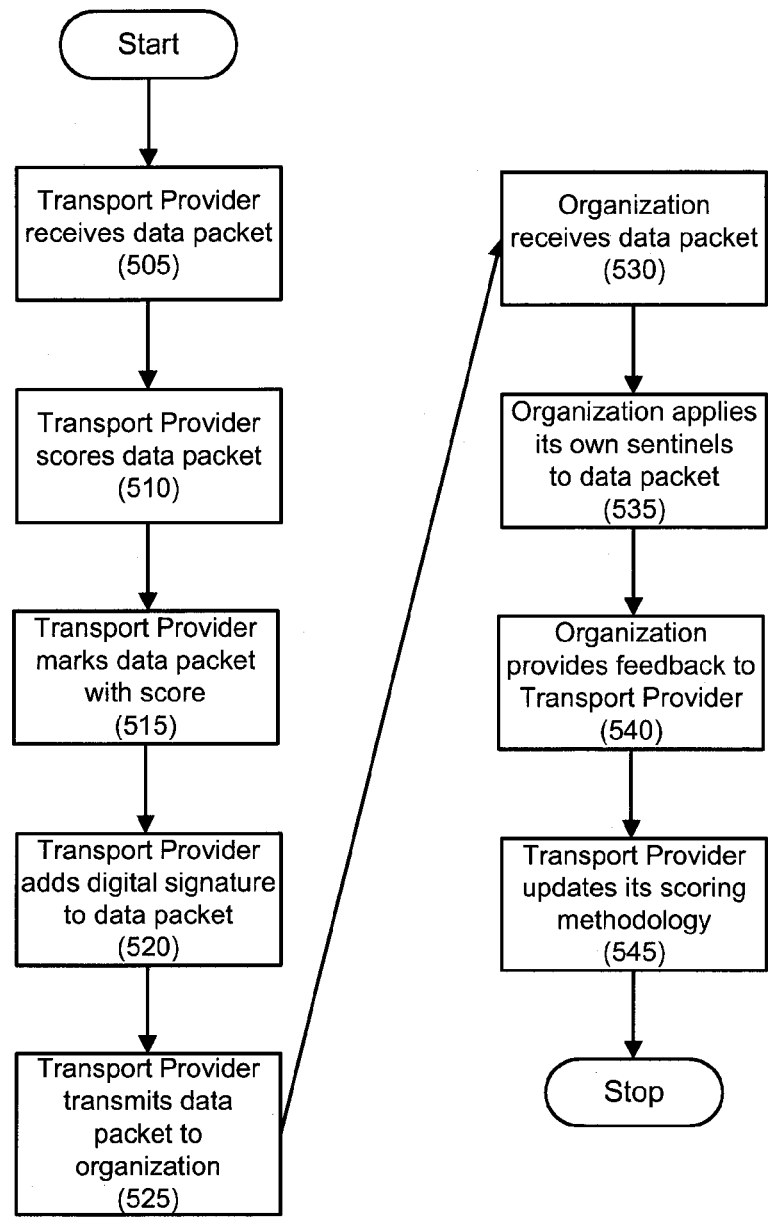
FIG. 5 is a flowchart depicting an example of a method for feedback in packet profiling according to another embodiment of the invention.

Referring to FIG. 5, a flowchart depicting an example of a method for feedback in packet profiling according to another embodiment of the invention is provided.

In step 505, the transport provider may receive an incoming data packet. This step may be similar to steps 210 and 410, above.

In step 510, the transport provider may score the data packet. This may be similar to step 230, above. This may include, for example, applying inspection sentinel(s) to the data packet, such as described in steps 220 and 420, above.

In step 515, the transport provider may mark the data packet with a score. This may be similar to step 240, above.

In step 520, the transport provider may add a digital signature to the data packet. This may be similar to that described with regard to step 240, above.

In step 525, the transport provider may transmit the data packet to the organization. This may be similar to step 250, above.

In step 530, the organization may receive the data packet. This may be similar to step 310, above.

In step 535, the organization may apply its own inspection sentinels to the data packet. This may be similar to step 330, above.

In step 540, the organization may provide data regarding the effectiveness of inspection sentinels, filtering, any undetected malicious data packets, false positives, etc. The data may further include an identification of the transport provider, an identification of any inspection sentinel(s) that were used, the source of the data packet, the intended recipient, etc. This data may be collected by a single organization, by multiple organizations, by a transport provider or multiple transport providers, by a third party, etc. The data may also be distributed, marketed, sold, etc. to transport providers, organizations, third parties, etc.

In step 545, the transport provider may receive the data. In one embodiment, the transport provider may not change its inspection sentinels and/or inspection methodology. In another embodiment, the transport provider may change its inspection sentinels and/or inspection methodology to account for any malicious data packets that were not scored and/or marked properly, and for any false positives. In still another embodiment, the transport provider may change its inspection sentinels and/or inspection methodology only to account for malicious data packets that were not scored and/or marked properly.

By the transport providers implementing this service, the organization may be able to decrease their DMZ footprint as the amount of data subject to deep-packet inspection may be reduced.

Hereinafter, general aspects of implementation of the systems and methods of the invention will be described.

The system of the invention or portions of the system of the invention may be in the form of a "processing machine," such as a general purpose computer, for example. As used herein, the term "processing machine" is to be understood to include at least one processor that uses at least one memory. The at least one memory stores a set of instructions. The instructions may be either permanently or temporarily stored in the memory or memories of the processing machine. The processor executes the instructions that are stored in the memory or memories in order to process data. The set of instructions may include various instructions that perform a particular task or tasks, such as those tasks described above. Such a set of instructions for performing a particular task may be characterized as a program, software program, or simply software.

As noted above, the processing machine executes the instructions that are stored in the memory or memories to process data. This processing of data may be in response to commands by a user or users of the processing machine, in response to previous processing, in response to a request by another processing machine and/or any other input, for example.

As noted above, the processing machine used to implement the invention may be a general purpose computer. However, the processing machine described above may also utilize any of a wide variety of other technologies including a special purpose computer, a computer system including, for example, a microcomputer, mini-computer or mainframe, a programmed microprocessor, a micro-controller, a peripheral integrated circuit element, a CSIC (Customer Specific Integrated Circuit) or ASIC (Application Specific Integrated Circuit) or other integrated circuit, a logic circuit, a digital signal processor, a programmable logic device such as a FPGA, PLD, PLA or PAL, or any other device or arrangement of devices that is capable of implementing the steps of the processes of the invention.

The processing machine used to implement the invention may utilize a suitable operating system. Thus, embodiments of the invention may include a processing machine running the Microsoft Windows™ 7 operating system, the Microsoft Windows™ Vista™ operating system, the Microsoft Windows™ XP™ operating system, the Microsoft Windows™ NT™ operating system, the Windows™ 2000 operating system, the Unix operating system, the Linux operating system, the Xenix operating system, the IBM AIX™ operating system, the Hewlett-Packard UX™ operating system, the Novell Netware™ operating system, the Sun Microsystems Solaris™ operating system, the OS/2™ operating system, the BeOS™ operating system, the Macintosh operating system, the Apache operating system, an OpenStep™ operating system or another operating system or platform.

It is appreciated that in order to practice the method of the invention as described above, it is not necessary that the processors and/or the memories of the processing machine be physically located in the same geographical place. That is, each of the processors and the memories used by the processing machine may be located in geographically distinct locations and connected so as to communicate in any suitable manner. Additionally, it is appreciated that each of the processor and/or the memory may be composed of different physical pieces of equipment. Accordingly, it is not necessary that the processor be one single piece of equipment in one location and that the memory be another single piece of equipment in another location. That is, it is contemplated that the processor may be two pieces of equipment in two different physical locations. The two distinct pieces of equipment may be connected in any suitable manner. Additionally, the memory may include two or more portions of memory in two or more physical locations. In one embodiment, virtual machines may be used.

To explain further, processing, as described above, is performed by various components and various memories. However, it is appreciated that the processing performed by two distinct components as described above may, in accordance with a further embodiment of the invention, be performed by a single component. Further, the processing performed by one distinct component as described above may be performed by two distinct components. In a similar manner, the memory storage performed by two distinct memory portions as described above may, in accordance with a further embodiment of the invention, be performed by a single memory portion. Further, the memory storage performed by one distinct memory portion as described above may be performed by two memory portions.

Further, various technologies may be used to provide communication between the various processors and/or memories, as well as to allow the processors and/or the memories of the invention to communicate with any other entity; i.e., so as to obtain further instructions or to access and use remote memory stores, for example. Such technologies used to provide such communication might include a network, the Internet, Intranet, Extranet, LAN, an Ethernet, wireless communication via cell tower or satellite, or any client server system that provides communication, for example. Such communications technologies may use any suitable protocol such as TCP/IP, UDP, or OSI, for example.

As described above, a set of instructions may be used in the processing of the invention. The set of instructions may be in the form of a program or software. The software may be in the form of system software or application software, for example. The software might also be in the form of a collection of separate programs, a program module within a larger program, or a portion of a program module, for example. The software used might also include modular programming in the form of object oriented programming. The software tells the processing machine what to do with the data being processed.

Further, it is appreciated that the instructions or set of instructions used in the implementation and operation of the invention may be in a suitable form such that the processing machine may read the instructions. For example, the instructions that form a program may be in the form of a suitable programming language, which is converted to machine language or object code to allow the processor or processors to read the instructions. That is, written lines of programming code or source code, in a particular programming language, are converted to machine language using a compiler, assembler or interpreter. The machine language is binary coded machine instructions that are specific to a particular type of processing machine, i.e., to a particular type of computer, for example. The computer understands the machine language.

Any suitable programming language may be used in accordance with the various embodiments of the invention. Illustratively, the programming language used may include assembly language, Ada, APL, Basic, C, C++, COBOL, dBase, Forth, Fortran, Java, Modula-2, Pascal, Prolog, REXX, Visual Basic, and/or JavaScript, for example. Further, it is not necessary that a single type of instruction or single programming language be utilized in conjunction with the operation of the system and method of the invention. Rather, any number of different programming languages may be utilized as is necessary and/or desirable.

Also, the instructions and/or data used in the practice of the invention may utilize any compression or encryption technique or algorithm, as may be desired. An encryption module might be used to encrypt data. Further, files or other data may be decrypted using a suitable decryption module, for example.

As described above, the invention may illustratively be embodied in the form of a processing machine, including a computer or computer system, for example, that includes at least one memory. It is to be appreciated that the set of instructions, i.e., the software for example, that enables the computer operating system to perform the operations described above may be contained on any of a wide variety of media or medium, as desired. Further, the data that is processed by the set of instructions might also be contained on any of a wide variety of media or medium. That is, the particular medium, i.e., the memory in the processing machine, utilized to hold the set of instructions and/or the data used in the invention may take on any of a variety of physical forms or transmissions, for example. Illustratively, the medium may be in the form of paper, paper transparencies, a compact disk, a DVD, an integrated circuit, a hard disk, a floppy disk, an optical disk, a magnetic tape, a RAM, a ROM, a PROM, an EPROM, a wire, a cable, a fiber, a communications channel, a satellite transmission, a memory card, a SIM card, or other remote transmission, as well as any other medium or source of data that may be read by the processors of the invention.

Further, the memory or memories used in the processing machine that implements the invention may be in any of a wide variety of forms to allow the memory to hold instructions, data, or other information, as is desired. Thus, the memory might be in the form of a database to hold data. The database might use any desired arrangement of files such as a flat file arrangement or a relational database arrangement, for example.

In the system and method of the invention, a variety of "user interfaces" may be utilized to allow a user to interface with the processing machine or machines that are used to implement the invention. As used herein, a user interface includes any hardware, software, or combination of hardware and software used by the processing machine that allows a user to interact with the processing machine. A user interface may be in the form of a dialogue screen for example. A user interface may also include any of a mouse, touch screen, keyboard, keypad, voice reader, voice recognizer, dialogue screen, menu box, list, checkbox, toggle switch, a pushbutton or any other device that allows a user to receive information regarding the operation of the processing machine as it processes a set of instructions and/or provides the processing machine with information. Accordingly, the user interface is any device that provides communication between a user and a processing machine. The information provided by the user to the processing machine through the user interface may be in the form of a command, a selection of data, or some other input, for example.

As discussed above, a user interface is utilized by the processing machine that performs a set of instructions such that the processing machine processes data for a user. The user interface is typically used by the processing machine for interacting with a user either to convey information or receive information from the user. However, it should be appreciated that in accordance with some embodiments of the system and method of the invention, it is not necessary that a human user actually interact with a user interface used by the processing machine of the invention. Rather, it is also contemplated that the user interface of the invention might interact, i.e., convey and receive information, with another processing machine, rather than a human user. Accordingly, the other processing machine might be characterized as a user. Further, it is contemplated that a user interface utilized in the system and method of the invention may interact partially with another processing machine or processing machines, while also interacting partially with a human user.

It will be readily understood by those persons skilled in the art that the present invention is susceptible to broad utility and application. Many embodiments and adaptations of the present invention other than those herein described, as well as many variations, modifications and equivalent arrangements, will be apparent from or reasonably suggested by the present invention and foregoing description thereof, without departing from the substance or scope of the invention.

Accordingly, while the present invention has been described here in detail in relation to its exemplary embodiments, it is to be understood that this disclosure is only illustrative and exemplary of the present invention and is made to provide an enabling disclosure of the invention. Accordingly, the foregoing disclosure is not intended to be construed or to limit the present invention or otherwise to exclude any other such embodiments, adaptations, variations, modifications or equivalent arrangements.

I claim:

1. A method for profiling incoming data packets for an organization, comprising:
   receiving, at an interface for a transport provider, a data packet intended for an organization;
   at least one computer processor analyzing the data packet by applying at least one inspection sentinel to the contents of the data packet;
   the at least one computer processor scoring the data packet based on the analysis;
   the at least one computer processor marking the data packet with the score;
   the at least one computer processor signing the data packet with a digital signature, the digital signature comprising an identification of the transport provider and at least one of a date of the scoring, a time of the scoring, an expiration of the scoring, and a classification of the packet; and
   the at least one computer processor transmitting the marked and digitally-signed data packet to the organization.

2. The method of claim 1, wherein a payload of the data packet is marked with the score.

3. The method of claim 1, further comprising:
   the at least one computer processor appending a second data packet to the scored data packet; and
   the at least one computer processor transmitting the scored data packet and the appended second data packet to the organization.

4. The method of claim 1, further comprising:
   the at least one computer processor storing the score at a location; and
   the at least one computer processor transmitting the data packet and a packet identifier for the stored score to the organization.

5. The method of claim 1, wherein data packets having a score above a predetermined threshold are sandboxed.

6. The method of claim 1, wherein data packets having a score below a first threshold are transmitted using a first data pipe, and data packets having a score above the first threshold are transmitted using a second data pipe.

7. The method of claim 1, wherein the score comprises a bit.

8. The method of claim 1, wherein the score comprises a plurality of bits.

9. The method of claim 1, wherein the at least one inspection sentinel is specific to the organization.

10. The method of claim 1, wherein the score is based on a risk of the data packet comprising at least some malicious data.

11. The method of claim 1, wherein the score is based on an attribute of the data packet.

12. The method of claim 1, wherein the at least one inspection sentinel searches for behavioral traits in the contents of the data packet.

13. The method of claim 1, further comprising:
    the at least one computer processor notifying the organization of the receipt of the data packet.

14. The method of claim 13, wherein the notification is provided using a transmission network that is different from the network over which the data packet and the appended score is transmitted.

* * * * *